United States Patent [19]
Foley et al.

[11] Patent Number: 6,048,699
[45] Date of Patent: Apr. 11, 2000

[54] METHOD OF FABRICATING BIO-CHIP ARRAYS

[75] Inventors: Barbara Foley, Phoenix; Fred V. Richard, Scottsdale; George N. Maracas, Phoenix; Huinan Yu, Phoenix; Fred Hickernell, Phoenix, all of Ariz.

[73] Assignee: Motorola, Inc., Schaumburg, Ill.

[21] Appl. No.: 09/174,605

[22] Filed: Oct. 19, 1998

[51] Int. Cl.⁷ .............................. C12Q 1/68; C12N 11/00; C07H 19/00; H04R 1/02; H01L 51/40

[52] U.S. Cl. .................. 435/6; 435/7.1; 435/174; 435/285.2; 435/287.2; 536/22.1; 536/23.1; 536/24.3; 536/24.31; 536/24.32; 536/24.33; 367/153; 367/155; 437/1

[58] Field of Search .......................... 435/5, 6, 7.1, 91.1, 435/91.2, 174, 285.2, 287.2; 536/22.1, 23.1, 24.3, 24.31, 24.32, 24.33; 367/153, 155; 437/1

[56] References Cited

PUBLICATIONS

Yang et al Analytica chimica Acta vol.346 pp. 259–275, 1997.

*Primary Examiner*—Kenneth R. Horlick
*Assistant Examiner*—Jeffrey Siew
*Attorney, Agent, or Firm*—William E. Koch

[57] ABSTRACT

A method of fabricating one or more arrays of bio-molecule test sites including providing a solution containing bio-molecule probes in contact with the surface of a substrate, using orthogonal acoustic waves to concentrate the bio-molecule probes at a node intersection, bonding the bio-molecule probes on the substrate at the node intersection to form a test site, and removing the solution leaving the bio-molecule probes attached to the surface at the test site. The steps are repeated as often as desired, using different bio-molecule probes, to produce one or more arrays of test sites.

21 Claims, 2 Drawing Sheets

METHOD OF FABRICATING BIO-CHIP ARRAYS

FIELD OF THE INVENTION

This invention relates to fabrication of molecular analyzers.

More particularly, the present invention relates a novel method of fabricating arrays of test sites on bio-chips.

BACKGROUND OF THE INVENTION

Identification of molecular structure has become very important in many industries. In particular, biological molecules such as nucleic acids and proteins are analyzed to form the basis of clinical diagnostic assays. The procedures utilized often involve large numbers of repetitive steps which consume large amounts of time. With the advent of large projects such as the human genome project, faster and less complex techniques are required.

Simpler and quicker analysis of molecules has been provided by the development of devices often referred to as bio-chips, which are arrays of test sites formed on a substrate. Each of the plurality of test sites includes probes therein to bond with target molecules from samples applied to the device. The binding of a molecule to a probe is noted, thereby identifying the molecule.

As the number of test sites in an array is increased, the complexity of fabricating the array or pluralities of arrays is greatly increased. Conventionally, placing bio-molecules as probes on specific test sites is time consuming, expensive, often lacks the desired accuracy and does not meet the desired size constraints. Placement of bio-molecules for probes is conventionally accomplished by in-situ synthesis using photolithography, which is very labor intensive with unsatisfactory accuracy; mechanical spotting, which is a slow process with the smallest test site size limited by the nature of the process; or chemical ink jetting, having an inaccuracy similar to in-situ synthesis and test site size limits similar to mechanical spotting. Furthermore, each of these techniques is generally limited to the formation of single arrays.

It would be highly advantageous, therefore, to remedy the foregoing and other deficiencies inherent in the prior art.

Accordingly, it is an object of the present invention to provide a new and improved apparatus and method for fabricating one or more arrays of test sites.

Another object of the present invention is to provide a method wherein a plurality of arrays of test sites are formed simultaneously.

And another object of the present invention is to provide a method using adjustable orthogonal acoustic waves to place bio-molecule probes at test sites.

SUMMARY OF THE INVENTION

Briefly, to achieve the desired objects of the instant invention, in accordance with a preferred embodiment thereof, provided is a method of fabricating one or more arrays of bio-molecule test sites including providing a solution containing bio-molecule probes in contact with the surface of a substrate, using orthogonal acoustic waves to concentrate the bio-molecule probes at one or more node intersections, bonding the bio-molecule probes on the substrate at the one or more node intersections to form one or more test sites, and removing the solution leaving the bio-molecule probes attached to the surface of the substrate at the test site or sites. The steps are repeated as often as desired, using solutions containing different bio-molecule probes, to produce one or more arrays each having one or more test sites. The positions of the test sites are changed by adjusting the frequencies of one or both of the orthogonal acoustic waves, which may be accomplished, for example, by adjusting the frequencies of transducers producing the acoustic waves and/or adjusting the longitudinal acoustic wave velocity of the solution.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which.

DETAILED DESCRIPTION OF THE PREFERRED EMBODIMENT

Figure 1:
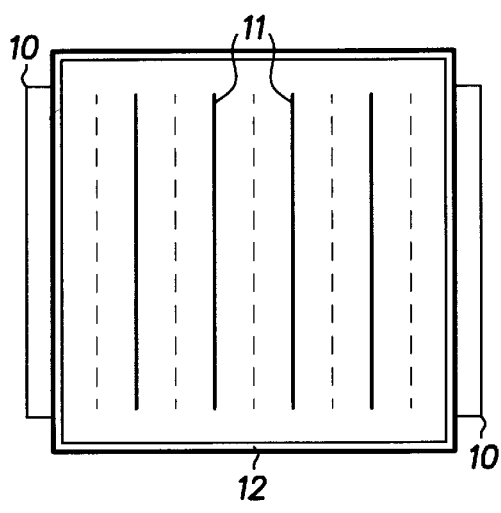
FIG. 1 is a simplified view in top plan of an adjustable transducer generating an acoustic wave with a plurality of acoustic nodes along an x axis within a solution.

Turning now to the drawings, attention is first directed to FIG. 1 which illustrates an adjustable transducer 10 generating an acoustic wave with a plurality of elongated acoustic nodes 11. It should be understood that transducer 10 can be a single structure or a pair of opposed transducers as illustrated. In the preferred embodiment, transducer 10 is mounted on opposed sides of a container 12 filled with a solution. Standing waves are generated in the solution with spaced apart and parallel acoustic nodes. The spacing of nodes 11 is determined by the frequency of the acoustic wave generated and the longitudinal acoustic wave velocity of the solution. It should be understood that the longitudinal acoustic wave velocity of the solution is dependent upon characteristics of the solution such as viscosity. By varying either or both of these features, acoustic nodes 11 can be produced as desired.

Figure 2:
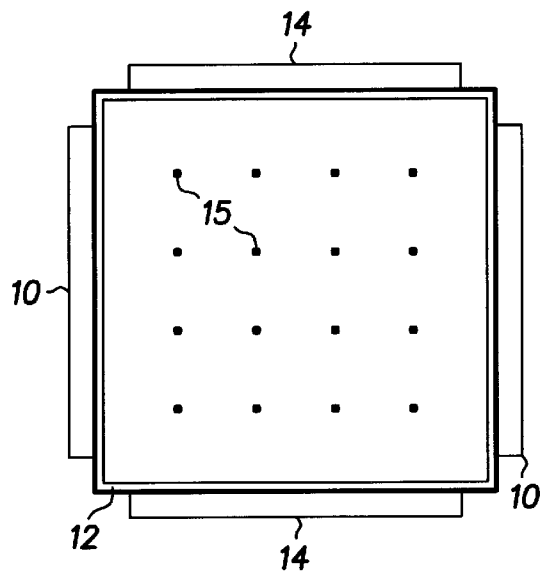
FIG. 2 is a simplified view in top plan of first and second adjustable transducers generating orthogonal acoustic waves in a solution.

Referring now to FIG. 2, another transducer 14 is employed generating an acoustic wave orthogonal to the acoustic wave generated by transducer 10. The acoustic wave generated by transducer 14 has a plurality of elongated acoustic nodes orthogonal to acoustic nodes 11. The intersections of these orthogonal acoustic nodes produces node intersections 15. It should be understood that transducer 14 can be a single structure or a pair of opposed transducers as illustrated. In the preferred embodiment, transducer 14 is mounted on opposed sides of container 12 filled with a solution. Standing waves are generated in the solution with spaced apart and parallel acoustic nodes. The spacing of the nodes is determined by the frequency of the acoustic wave generated and the longitudinal acoustic wave velocity of the solution.

Figure 3:
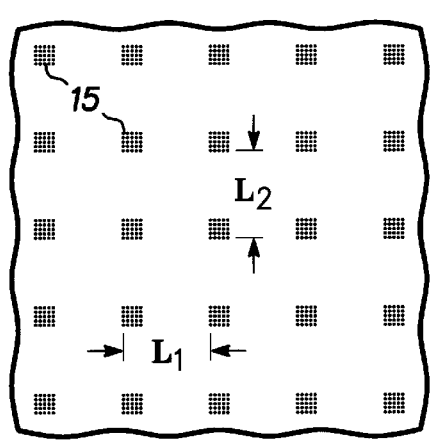
FIG. 3 is an enlarged view in top plan illustrating first and second orthogonal acoustic waves in a solution with a plurality of acoustic nodes.

With additional reference to FIG. 3, and assuming container 12 is formed with dimensions in a range of from 0.5 cm by 0.5 cm to 1.0 cm by 1.0 cm, the spacing between node intersections L1 and/or L2 will be in a range of from 50 to 150 microns. Assuming a solution similar to water with a longitudinal acoustic wave velocity of near 1500 m/s and a wavelength of 100 microns, the corresponding frequency is:

$$f = v/\lambda = 1500/100 \times 10^{-6} = 15 \times 10^6 \text{ Hz} = 15 \text{ MHz}$$

Assuming 150 microns wavelength spacing, the corresponding frequency is 10 MHz and at 300 microns wavelength spacing, the corresponding frequency is 5 MHz. Thus, the transducer frequency is preferably in the range of 5 to 15 MHz, although different frequencies can be used for different applications. If a 5 MHz transducer is used with a 300 micron spacing across an area of 1 cm², the number N of node intersections is:

$$N = 10^{-2}/300 \times 10^{-6} = 10^4/300 \approx 33 \text{ points/cm or } 1100 \text{ points/cm}^2$$

So depending on the size of container 12 and the frequency of transducers 10 and 14, the number of node intersections can be determined.

Figure 4:
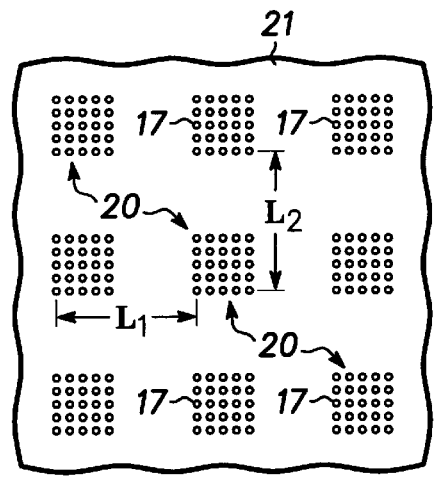
FIG. 4 is a greatly enlarged view in top plan illustrating a plurality of similar arrays of test sites positioned at regular intervals on a substrate.

Still referring to FIG. 3, with additional reference to FIG. 4, node intersections 15 correspond to single test sites 17 in each of a plurality of arrays. Here it should be understood that FIG. 4 illustrates a plurality of test site arrays 20 positioned on a substrate 21. The positions of test sites 17 are changed by altering the position of the node intersections 15. By adjusting the frequencies of one or both of the orthogonal acoustic waves, which may be accomplished, for example, by adjusting the frequencies of transducers 10 and 14 producing the acoustic waves and/or adjusting the longitudinal acoustic wave velocity of the solution in container 12, the acoustic nodes of the waves and thus the node intersections are altered.

It is possible that, for a given set of parameters, including the transducer frequency, the spacing between test sites 17 of test site arrays 20 and the number of test site arrays 20 across substrate 21, there will be an offset of the spacing between test sites 17 from one edge of substrate 21 to the other edge of substrate 21. If a detection mechanism for test site arrays 20 requires that test site arrays 20 have identical spacing, the following techniques can be used to compensate or prevent offset. 1) The standing wave pattern of transducer pairs can be shifted by prebiasing the transducers appropriately or 2) the frequency of the transducer pairs remains constant and substrate 21 is repositioned by the appropriate amount and in the appropriate direction to produce correctly spaced test site arrays 20.

Test sites 17 have groups of probes (not shown) coupled thereto. Each test site 17 contains a plurality of probes which are capable of binding to specific molecular structures. The molecular structure can comprise, for example, biopolymers such as polynucleotides, protein, DNA, RNA, cells, enzymes, antibodies, antigens, etc. In the case of DNA or RNA testing, the probes can comprise, for example, oligonucleotides. All of the probes at a given test site 17 are identical. The probes in respective test sites differ in sequence for simultaneous detection of a plurality of different target molecules within a single test site array 20.

Still referring to FIG. 4, in a preferred method of fabrication, a solution carrying bio-molecules which will act as probe molecules, such as single stranded DNA molecules, is positioned on substrate 21 in which the node intersections 15 are formed. The bio-molecules within the solution are moved by the wave action at a given frequency to concentrate at node intersections 15 corresponding to individual test sites 17 within each of the test site arrays 20. While the probe molecules can be bound to test sites 17 in any manner, in a preferred embodiment, the probe molecules include a monomer which polymerizes with material at the surface of substrate 21. The solution is then removed.

The fabrication process continues by providing a second solution containing a plurality of second probe molecules. One or both of transponders 10 and 14 are adjusted to change the frequency, thus shifting node intersection 15 to another test site 17 of each test site array 20. The bio-molecules within the second solution are moved by the wave action at the selected frequency to concentrate at node intersections 15 corresponding to the next test site 17 within each of the test site arrays 20. The probe molecules are bound to substrate 21 as described above, and the solution is removed.

This process is repeated as many times as needed to produce a plurality of chips for use in bio-molecule analyzers. These chips are then separated using conventional processes such as scribing, sawing etc. In this fashion, a bio-chip having a one or two dimensional array of test sites can be easily fashioned with a reduction in labor intensity, greater accuracy, quicker processing and the ability to build very small test sites.

Figure 5:
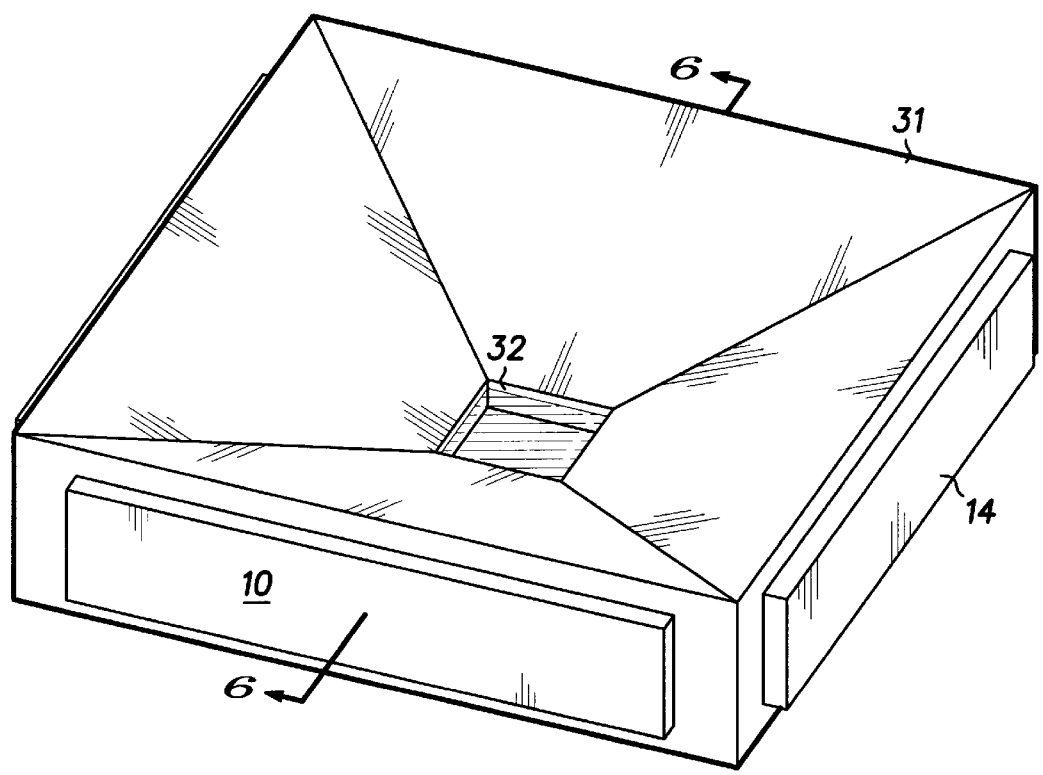
FIG. 5 is an enlarged isometric view of apparatus for fabricating arrays of bio-molecule test sites in accordance with the present invention.
Figure 6:
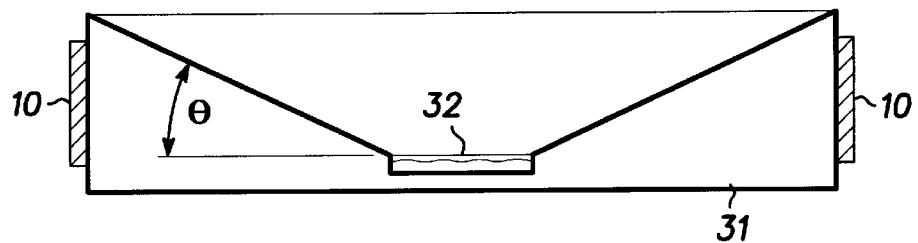
FIG. 6 is a sectional view as seen from the line 6—6 in FIG. 5.

Turning now to FIGS. 5 and 6, apparatus for fabricating bio-chips, generally designated 30, is illustrated. The dimensions shown are not necessarily accurate and are intended for purposes of better understanding the structure. Apparatus 30 includes a tub 31 having a fluid container 32 for receiving substrate 21 and the various fluids used during fabrication of bio-chips. Transponders 10 and 14 are affixed to the sides of tub 31. Owing to the fact that the depth of the fluid is considerably less than the height of transponders 10 and 14, the sides of tub 31 are tapered from transponders 10 and 14 to fluid container 32, allowing a focus of the acoustic waves into the solution. There are other possible configurations which preserve the area of transducers 10 and 14 for good impedance matching and focusing the ultrasonic energy into the fluid in fluid container 32. For example, a longer transducer and a narrower width.

Thus, provided is a new and improved apparatus and method for fabricating one or more arrays of test sites simultaneously using adjustable orthogonal acoustic waves to place bio-molecule probes at test sites.

Various modifications and changes to the embodiments herein chosen for purposes of illustration will readily occur to those skilled in the art. Other modifications and variations may be made by those skilled in the art without departing from the scope of the invention as defined by the following claims.

Having fully described and disclosed the present invention and preferred embodiments thereof in such clear and concise terms as to enable those skilled in the art to understand and practice same, the invention claimed is:

1. A method of fabricating arrays of bio-molecule test sites including the steps of:

providing a solution containing bio-molecule probes in contact with the surface of a substrate;

using orthogonal acoustic waves to concentrate the bio-molecule probes at a node intersection; and bonding the bio-molecule probes on the substrate at the node intersection to form a test site.

2. A method of fabricating an array of bio-molecule test sites comprising the steps of:

providing a substrate having a surface;

providing a first solution containing first bio-molecule probes;

placing the first solution in contact with the surface of the substrate;

forming a first node intersection adjacent the surface in the first solution using orthogonal acoustic waves, thereby concentrating the first bio-molecule probes at the first node intersection;

bonding the first bio-molecule probes on the surface at the first node intersection to form a first test site;

removing the first solution leaving the first bio-molecule probes attached to the surface at the first test site;

providing a second solution containing second bio-molecule probes;

placing the second solution in contact with the surface of the substrate;

forming a second node intersection adjacent the surface in the second solution, spaced from the first node intersection, using orthogonal acoustic waves, thereby concentrating the second bio-molecule probes at the second node intersection;

bonding the second bio-molecule probes on the surface at the second node intersection to form a second test site; and removing the second solution leaving the second bio-molecule probes attached to the surface at the second test site.

3. A method as claimed in claim 2 wherein the steps of forming the first and second node intersections includes transmitting orthogonal acoustic waves through the first and second solutions, respectively, and altering frequencies thereof to alter the respective positions of the first and second node intersections.

4. A method as claimed in claim 2 wherein the steps of forming the first and second node intersections includes providing a first adjustable transducer generating an acoustic wave along an x axis and a second adjustable transducer generating an acoustic wave along a y axis orthogonal to the x axis.

5. A method as claimed in claim 4 wherein the step of altering the frequencies of the orthogonal acoustic waves includes altering longitudinal acoustic wave velocity of the first and second solutions.

6. A method as claimed in claim 4 wherein the step of altering the frequencies of the orthogonal acoustic waves includes altering the frequencies of the acoustic waves generated by the first and second transducers.

7. A method as claimed in claim 4 wherein the steps of forming first and second test sites are repeated to form a two dimensional array of test sites by adjusting one of the first adjustable transducer to alter the acoustic wave along the x axis and the second adjustable transducer to alter the acoustic wave along a y axis orthogonal to the x axis.

8. A method as claimed in claim 4 wherein the step of providing a first adjustable transducer includes generating an acoustic wave along an x axis having a plurality of acoustic nodes, and the step of providing a second adjustable transducer includes generating an acoustic wave along a y axis having a plurality of acoustic nodes orthogonal to the x axis to produce a plurality of arrays of test sites at node intersections thereof.

9. A method as claimed in claim 4 wherein the step of providing a first adjustable transducer generating an acoustic wave along an x axis and a second adjustable transducer generating an acoustic wave along a y axis includes providing surface acoustic wave transducers.

10. A method of fabricating a plurality of arrays of bio-molecule test sites comprising the steps of:

providing a substrate having a surface;

providing a first solution containing first bio-molecule probes;

placing the first solution in contact with the surface of the substrate;

generating a first acoustic wave, having a plurality of acoustic nodes, within the first solution along an x axis and a second acoustic wave, having a plurality of acoustic nodes, within the first solution along a y axis orthogonal to the x axis to form a plurality of first node intersections adjacent the surface in the first solution at the intersections of the acoustic nodes of the first and second acoustic waves, thereby concentrating the first bio-molecule probes at the first node intersections;

bonding the first bio-molecule probes on the surface at the first node intersections to form a first plurality of test sites;

removing the first solution leaving the first bio-molecule probes attached to the surface at the first plurality of test sites;

providing a second solution containing second bio-molecule probes;

placing the second solution in contact with the surface of the substrate;

generating a third acoustic wave, having a plurality of acoustic nodes, within the second solution along an x axis and a fourth acoustic wave, having a plurality of acoustic nodes, within the second solution along a y axis orthogonal to the x axis to form a plurality of second node intersections adjacent the surface in the second solution at the intersections of the acoustic nodes of the third and fourth acoustic waves, thereby concentrating the second bio-molecule probes at the second node intersections;

bonding the second bio-molecule probes on the surface at the second node intersections to form a second plurality of test sites; and removing the second solution leaving the second bio-molecule probes attached to the surface at the second plurality of test sites.

11. A method as claimed in claim 10 wherein the steps of generating first, second, third, and fourth acoustic waves includes generating first, second, third, and fourth acoustic waves in a frequency range of approximately 5 MHz to 15 MHz.

12. A method as claimed in claim 10 wherein the step of forming the first and second pluralities of test sites includes forming each of the test sites from the first and second pluralities of test sites in a different one of a plurality of arrays.

13. A method as claimed in claim 10 wherein the steps of generating the first and second, and third and fourth acoustic waves includes transmitting orthogonal acoustic waves through the first and second solutions, respectively, and altering frequencies thereof to alter the respective positions of the pluralities of first and second node intersections.

14. A method as claimed in claim 13 wherein the step of altering the frequencies of the first and second, and third and fourth acoustic waves includes altering longitudinal acoustic wave velocity of the first and second solutions.

15. A method of fabricating a plurality of arrays of bio-molecule test sites comprising the steps of:

providing a substrate having a surface;

providing a first solution containing first bio-molecule probes;

placing the first solution in contact with the surface of the substrate;

providing a first adjustable transducer generating a first acoustic wave, having a plurality of acoustic nodes, within the first solution along an x axis and a second adjustable transducer generating a second acoustic wave, having a plurality of acoustic nodes, within the first solution along a y axis orthogonal to the x axis to form a plurality of first node intersections adjacent the surface in the first solution at the intersections of the acoustic nodes of the first and second acoustic waves, thereby concentrating the first bio-molecule probes at the first node intersections;

bonding the first bio-molecule probes on the surface at the first node intersections to form first test sites;

removing the first solution leaving the first bio-molecule probes attached to the surface at the first test sites;

providing a second solution containing second bio-molecule probes;

placing the second solution in contact with the surface of the substrate;

adjusting the first adjustable transducer to generate a third acoustic wave, having a plurality of acoustic nodes, within the second solution along an x axis and adjusting the second adjustable transducer to generate a fourth acoustic wave, having a plurality of acoustic nodes, within the second solution along a y axis orthogonal to the x axis to form a plurality of second node intersections adjacent the surface in the second solution at the intersections of the acoustic nodes of the third and fourth acoustic waves, thereby concentrating the second bio-molecule probes at the second node intersections;

bonding the second bio-molecule probes on the surface at the second node intersections to form a second plurality of test sites; and removing the second solution leaving the second bio-molecule molecule probes attached to the surface at the second plurality of test sites.

16. A method as claimed in claim 15 wherein the step of forming the first and second pluralities of test sites includes forming each of the test sites from the first and second pluralities of test sites in a different one of a plurality of arrays.

17. A method as claimed in claim 15 wherein the steps of generating the first and second, and third and fourth acoustic waves includes transmitting orthogonal acoustic waves through the first and second solutions, respectively, and altering frequencies thereof to alter the respective positions of the pluralities of first and second node intersections.

18. A method as claimed in claim 17 wherein the step of altering the frequencies of the first and second, and third and fourth acoustic waves includes altering longitudinal acoustic wave velocity of the first and second solutions.

19. A method as claimed in claim 17 wherein the step of altering the frequencies of the first and second, and third and fourth acoustic waves includes altering the frequencies of the acoustic waves generated by the first and second transducers.

20. A method as claimed in claim 15 wherein the steps of providing the first solution containing the first bio-molecule probes, placing the first solution in contact with the surface of the substrate, providing a first adjustable transducer generating a first acoustic wave and a second adjustable transducer generating a second acoustic wave, bonding the first bio-molecule probes, and removing the first solution are repeated with solutions containing different bio-molecule probes and different orthogonal acoustic waves having node intersections at different locations to produce a plurality of arrays of test sites.

21. A method as claimed in claim 20 further including a step of separating the plurality of arrays of test sites into similar individual arrays.

* * * * *